United States Patent [19]
Forber

[11] Patent Number: 6,039,744
[45] Date of Patent: Mar. 21, 2000

[54] ASSEMBLY FOR POSITIONING AN IMPLANT IN AN INTERNAL PASSAGEWAY OF A BODY

[75] Inventor: Simon John Forber, Yversay, France

[73] Assignee: B. Braun Celsa, Boulogne-Billancourt, France

[21] Appl. No.: 09/205,610

[22] Filed: Dec. 4, 1998

[30] Foreign Application Priority Data

Dec. 19, 1997 [FR] France .................................. 97 16147

[51] Int. Cl.[7] .................................................. A61M 25/01
[52] U.S. Cl. .......................................................... 606/108
[58] Field of Search ........................... 606/1, 108, 106, 606/109, 192, 194, 195, 198, 200, 209; 623/1, 12

[56] References Cited

U.S. PATENT DOCUMENTS

| | | | |
|---|---|---|---|
| 4,425,908 | 1/1984 | Simon | 606/200 |
| 5,053,041 | 10/1991 | Ansari et al. | 606/1 |
| 5,634,942 | 6/1997 | Chevillon et al. | |
| 5,669,924 | 9/1997 | Shaknovich | 606/108 |
| 5,746,769 | 5/1998 | Ton et al. | 606/198 |
| 5,755,735 | 5/1998 | Richter et al. | 606/194 |
| 5,755,790 | 5/1998 | Chevillon et al. | |
| 5,800,457 | 9/1998 | Gelbfish | 606/200 |

FOREIGN PATENT DOCUMENTS

| | | |
|---|---|---|
| 0696447 | 2/1996 | European Pat. Off. |
| 0737451 | 10/1996 | European Pat. Off. |

*Primary Examiner*—Jeffrey A. Smith
*Assistant Examiner*—Eduardo C. Robert
*Attorney, Agent, or Firm*—Rothwell, Figg, Ernst & Kurz, P.C.

[57] ABSTRACT

The invention is an assembly for positioning an implant that has an axis and at least one axial tubular region having an inside diameter. More specifically, the assembly positions the implant into an internal passageway in a body, such as a blood vessel. The assembly has two removable elements, both having a predetermined cross-section. At the distal end of the first element of the assembly is a lateral protuberance having a radial length. The assembly is further characterized in that the cumulative cross-section dimension of the two elements away from their distal ends and the radial length of the lateral protuberance are both smaller than the inside diameter of the axial tubular region of the implant.

11 Claims, 5 Drawing Sheets

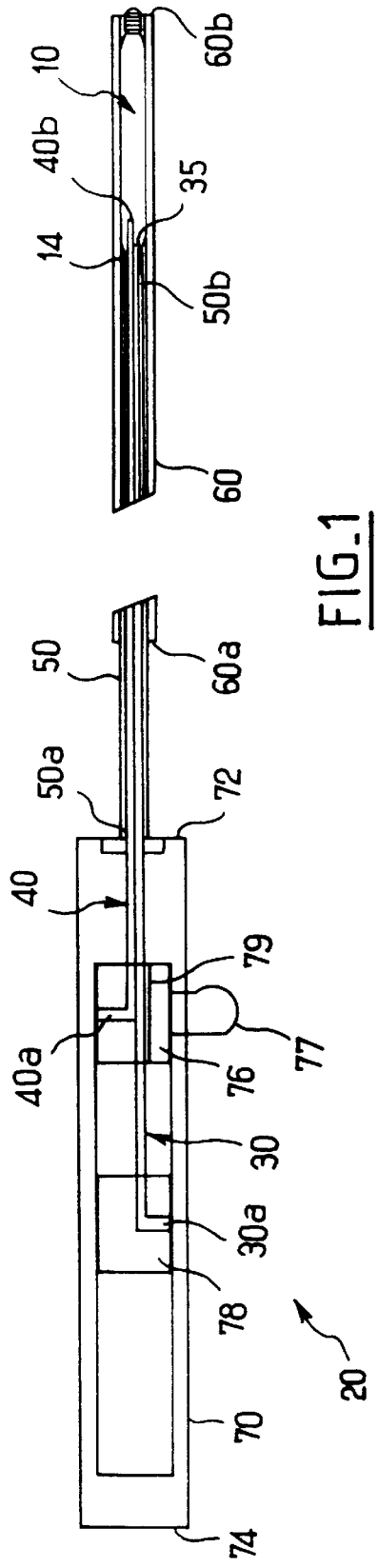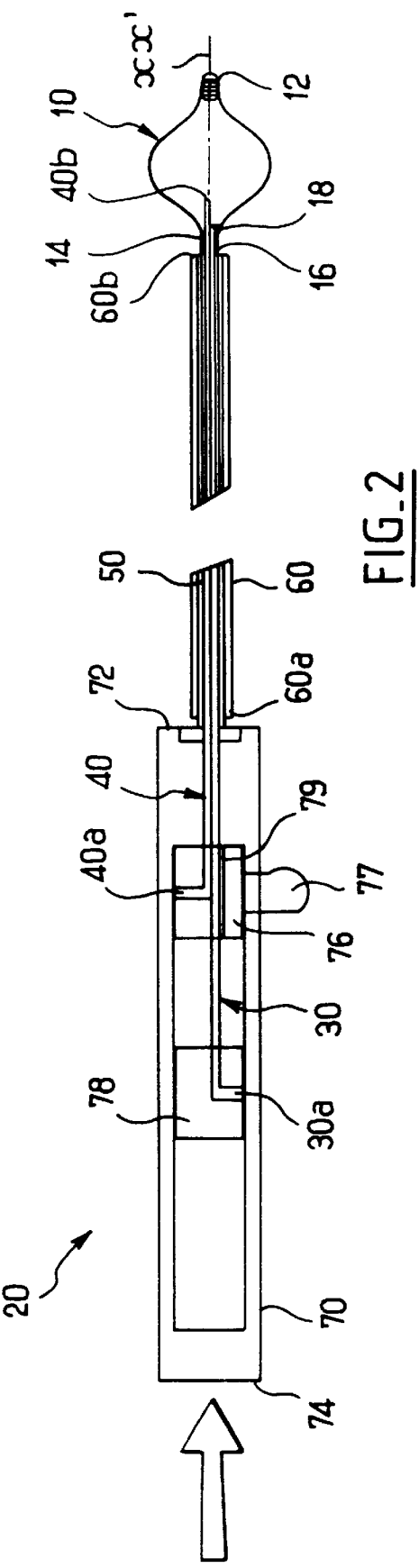

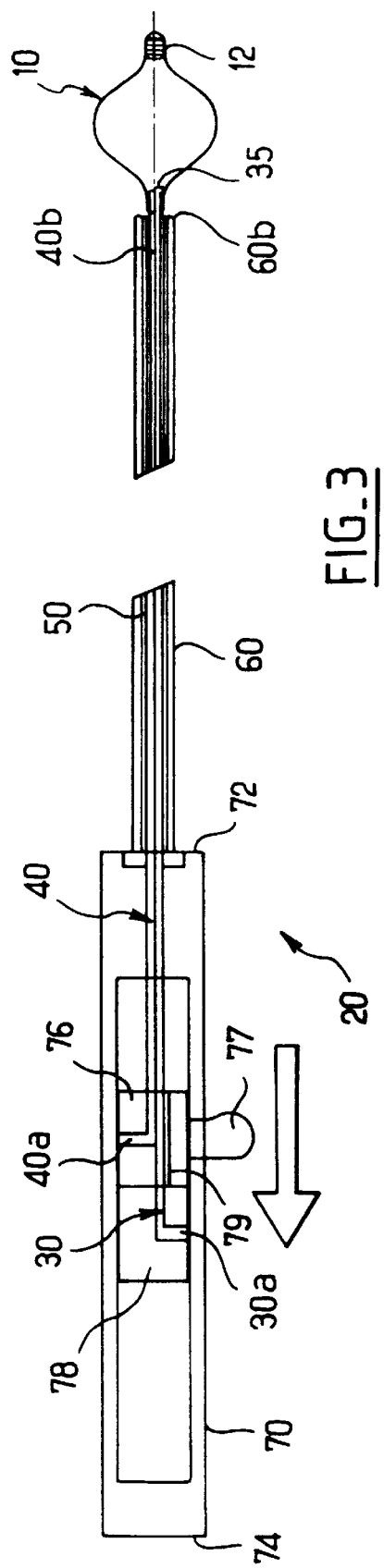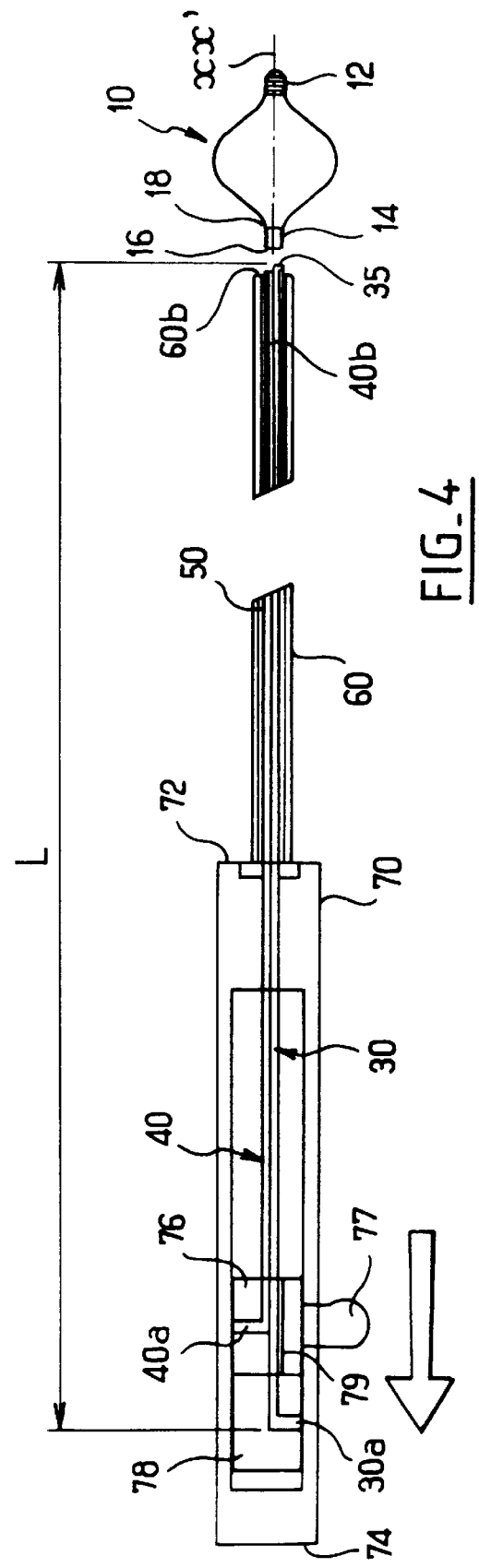
FIG_3
FIG_4

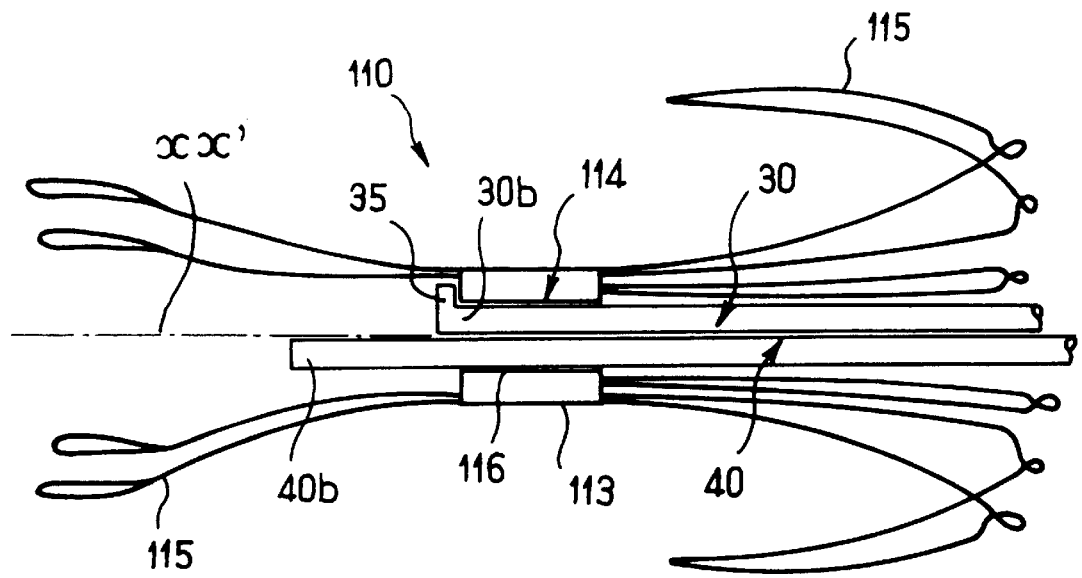
FIG._6
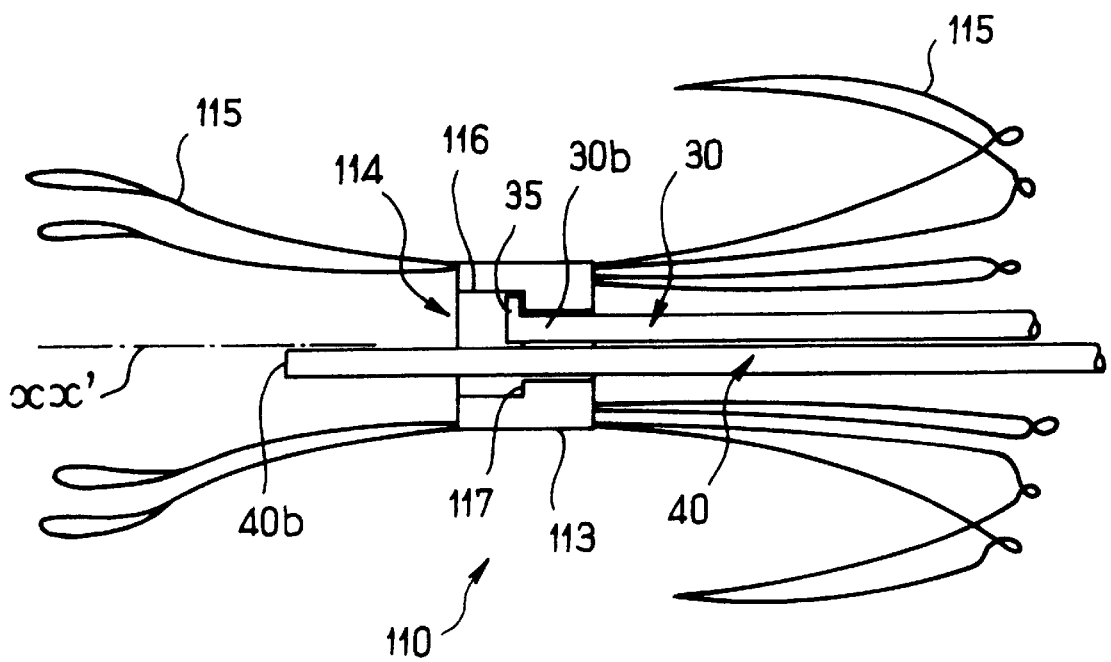
FIG._7

ASSEMBLY FOR POSITIONING AN IMPLANT IN AN INTERNAL PASSAGEWAY OF A BODY

The field of the invention is that of devices used for positioning endoprostheses in an internal passageway of a body, and especially in a blood vessel.

BACKGROUND OF THE INVENTION

Endoprostheses have an axis and comprise a structure suitable for adopting a first, radially deployed, state in a situation implanted in the passageway, or a second, radially restricted, state in a positioning situation, for example inside an intraluminal introduction sleeve. In practice, such implants may comprise especially an occlusion device or vascular device, a blood filter having limbs, or even a stent for the treatment of stenosis, or a prosthesis for the treatment of an aneurysm.

At present, difficulties are sometimes encountered in placing an implant in its closed state inside its introduction sleeve, especially when the implant is small. Likewise, when an implant of the temporary or temporary/permanent type is positioned inside a passageway, it is necessary to be able to hold or detach the implant with respect to its introduction system, and even to be able to recover it after having released it.

SUMMARY OF THE INVENTION

The invention proposes a simple and reliable solution which is adaptable to various types of implant, is easy to implement and is inexpensive.

According to that solution, the device for retaining or releasing the implant comprises at least a first and a second removable elongate element, which elements have a predetermined cross-section and extend substantially parallel to one another, the first element having, towards a distal end, a lateral protuberance having a radial length, while the other element has no such protuberance, the cumulative cross-sectional dimension of the two elements away from their distal end, and the radial length of the lateral protuberance, being smaller than the inside diameter of the tubular region of the implant so that the elements pass through at their distal end, in a situation of positioning the implant in the passageway, while being adapted to be withdrawn therefrom after positioning has taken place.

In order to improve the retention of the implant by the retention/release device, and with the purpose of facilitating the use of the device, the first and second elongate elements are preferably in the form of two long wires arranged slidably in a catheter with the protuberance of the first element then being located outside the catheter, the catheter and the wires being sufficiently long to be manoeuvred from outside the body of the patient, while the implant is in the passageway.

In order to improve the axial sliding of the elongate elements inside the sleeve without impairing the retention of the implant, at least one of the two wires preferably has over most of its length a cross-section which is strictly smaller than half the inside diameter of the catheter, it then being possible for the other wire to have over its entire length a cross-section smaller than or equal to half the inside diameter of the catheter, so that the sum of the cross-sections of the two wires is strictly smaller than the inside diameter of the catheter.

With the same aim, the two wires also advantageously have a circular cross-section and each has a diameter strictly smaller than half the inside diameter of the catheter over their entire length with the exception of a region close to their distal end where their diameter is preferably greater than or equal to half the inside diameter of the catheter.

Still with the aim of facilitating the positioning of the implant, the assembly may also comprise a sleeve which has an inside diameter which is greater than the outside diameter of the catheter and of the tubular region of the implant and which is suitable for accommodating the implant in its radially restricted state, the catheter and the wires then constituting a means of manoeuvre sufficiently rigid to provide for axial movement of the implant in order to position it in the passageway.

Still with the same aim and in order to promote the maintenance of the implant in its held position, while the distal end of the elongate elements is engaged through the tubular region of the implant, the catheter can be placed substantially against a proximal surface of that region while the lateral protuberance of the first element can be placed against a distal surface of said region.

In order to facilitate the retention of the implant before it is detached from its positioning device, the first element is preferably in the form of a substantially rectilinear rod which is curved at its distal end, forming an angle of approximately from 45° to 90° with the rod, to form a short hook.

With the aim of improving the remote positioning of the implant, the assembly may also comprise a grip having a front end beyond which the elongate elements extend, each element being secured to an axial slide, and the first slide, to which the second element is secured, being arranged in front of that to which the first element is secured. In particular, the first slide is preferably provided with a manoeuvring arm in order to be accessible to the user's hand, while the second slide is not accessible from outside the grip.

The invention can be applied especially in cases where the implant is a blood filter, and preferably a filter suitable for being implanted either temporarily or temporarily then permanently, after the withdrawal of the holding/release device from the tubular region of the filter.

According to another consideration, the implant may be a vascular atherectomy or occlusion device.

BRIEF DESCRIPTION OF THE DRAWINGS

The invention will emerge even more clearly from the following description which is given with reference to the appended drawings in which:

FIGS. 1 to 4 show, in section, an assembly according to the present invention and the various positioning steps, FIG. 6 shows a second embodiment for the implantation of a blood filter of the temporary or temporary/permanent type, FIG. 7 is a variant of FIG. 6.

DETAILED DESCRIPTION OF THE PREFERRED EMBODIMENTS

Figure 5:
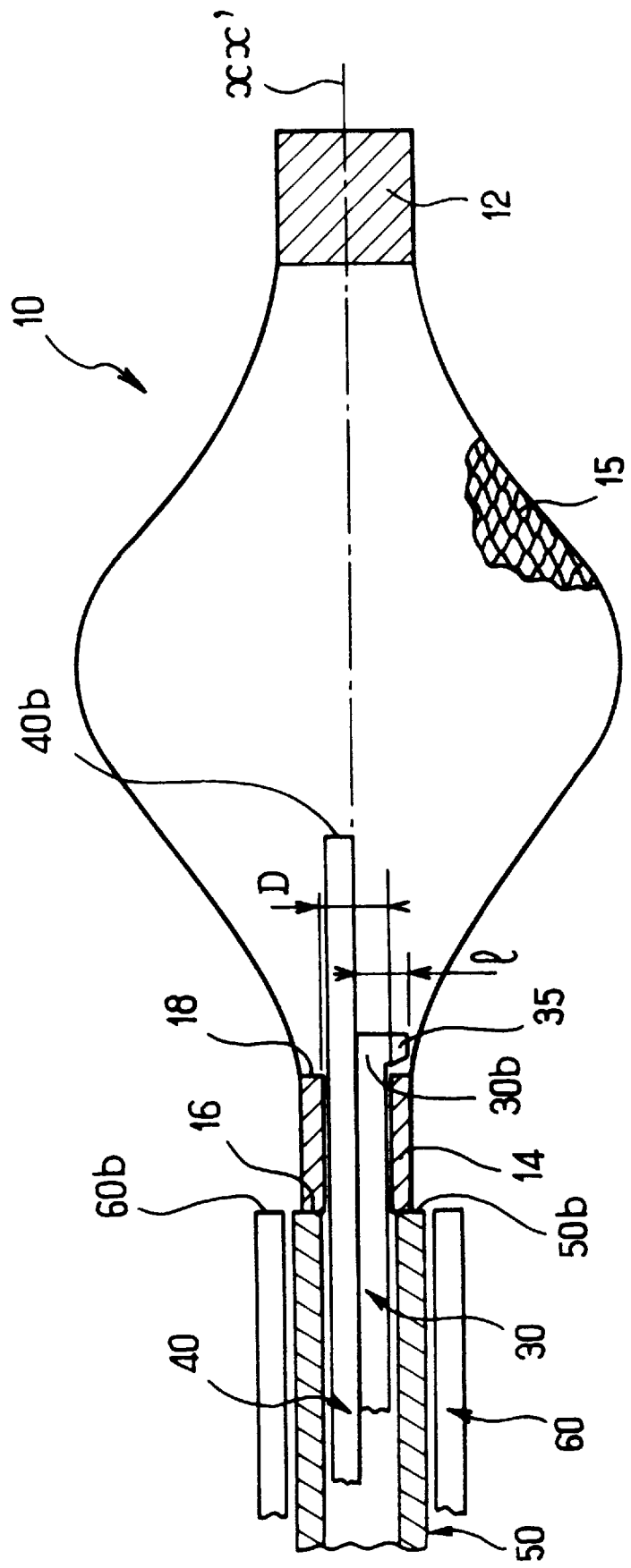
FIG. 5 shows in detail the tubular region of the implant and a portion of its positioning device.

An endoprosthesis 10, which is in this case a vascular occlusion device (which can also act as a blood filter), is represented in FIGS. 1 to 5. The endoprosthesis 10 has a longitudinal axis xx' and comprises at least one axial ring (or collar) 14 having an inside diameter D, a proximal end 16 and a distal end 18.

The implant 10 also comprises a structure 15 suitable for adopting a first, radially deployed, state in a situation implanted in the passageway (FIGS. 2 to 4), or a second, radially restricted, state in a positioning situation (FIG. 1), for example a structure having woven filaments. In its radially deployed state, it assumes the form of a basket bulging in the central portion and closed at its distal and proximal ends by a solid sleeve 12 and by the hollow ring 14, respectively.

A device 20 for retaining or releasing the implant 10 is also shown in those Figures. The device 20 comprises at least a first element 30 and a second element 40. The elements 30 and 40 are elongate and movable substantially along the axis xx' and they extend substantially parallel to one another. The first element 30 has, at a distal end 30b, a lateral protuberance 35, typically a substantially 90° curve forming a short hook relative to the axial length L of the rod 30 (see FIG. 5), while the second element 40 has no such protuberance, that is to say, it is in this particular case exclusively rectilinear. In particular, the elongate elements 30 and 40 are in the form of two wires (or filaments) having a circular cross-section (of a diameter of the order of from one to a few tenths of a millimeter), which are substantially straight and preferably of metal, although they may also be produced from plastics or in the form of a helix.

The sum of the diameters of the two rods 30 and 40, away from their distal end 30b/40b, and the radial length l of the hook 35, are smaller than the inside diameter D of the ring 14 of the implant 10 so that the elements 30 and 40 can pass through the ring at their distal end 30b/40b while being adapted to be withdrawn therefrom once the implant 10 is in place in the passageway.

The two rods (or wires) 30/40 are arranged in a catheter 50 inside which they can slide axially, the hook 35 of the first wire 30 being arranged outside the catheter 50, beyond its distal end 50b. The wires are sufficiently long (typically from 10 to 20 cm) to be manipulated from a distance, that is to say, from outside the patient's body, with a view to enabling the implant 10 to be positioned inside the passageway concerned.

The introduction assembly also comprises a flexible sleeve 60 which is produced from biocompatible plastics material and which has an inside diameter greater than the outside diameter of the catheter and than that of the endoprosthesis 10 in the radially closed state thereof, as shown in FIG. 1. The sleeve 60 is slightly shorter than the catheter 50 and has a distal end 60b and a proximal end 60a.

The assembly also comprises a grip 70 having a front end 72 to which the catheter 50 is secured and beyond which the wires 30 and 40 extend, and also a rear end 74. Inside the grip 70, the wire 40 is connected to a first slide 76 and the wire 30 is connected to a second slide 78, the first slide 76 being arranged in front of the second. The first slide 76 is provided with a manoeuvring arm 77 projecting from the grip 70, while the second slide 78 is not accessible from outside the grip 70. The first wire 30 can slide through a hole 79 in the first slide 76.

With reference to FIGS. 1 to 4, we shall now describe the steps involved in positioning an implant 10.

It will be assumed that the implantation is effected endoluminally (for example by the so-called "SELDINGER" method).

In FIG. 1, the implant 10 is introduced into the sleeve 60 in its radially closed state, towards the sleeve's distal end 60b. The catheter 50 is advanced in the sleeve 60 so that its distal end 50b is supported against the proximal end 16 of the ring 14. The grip 70 is outside the patient's body and the slides 76 and 78 are sufficiently advanced inside the grip 70 for the second wire 40 to be located inside the implant 10, beyond the ring 14, and for the hook 35 to be supported behind the ring (at its distal end 18). In that arrangement, the proximal end 60a of the sleeve is positioned away from the front end 72 of the grip.

The sleeve 60 (FIG. 2) is then pulled back while the grip 70 is held tightly (or the grip 70 is advanced while the sleeve 60 is held tightly) so that the proximal end 60a of the sleeve 60 approaches the front end 72 of the grip. As a result of that approach, the catheter 50 pushes the implant 10 axially and causes it to move out of the sleeve 60. The endoprosthesis 10 is then deployed radially inside the blood vessel concerned. During that operation, the slides 76/78 are held in place axially in the grip 70, for example by means of a catch system (not shown).

If the endoprosthesis 10 is then to be withdrawn or moved, it is necessary only to push back the grip 70 (without interfering with the slides) in such a manner as to cause it to return into the inside of the sleeve 60, and then to move the sleeve.

In order to release the implant 10, the first slide 76 is pulled back (FIG. 3) into the inside of the grip 70 by means of the manoeuvring arm 77, until it comes into contact with the second slide 78. The second wire 40 is then pulled rearwardly until it comes out of the ring 14. Thus, only the first wire 30 still remains in the implant 10, which is retained on the positioning device 20 by means of the hook 35.

In order to release the implant 10 completely, the first slide 76 continues to be pulled back (FIG. 4), which causes the second slide to move back, thus pulling the two wires 30 and 40 rearwards. The hook 35 therefore passes through the ring 14, thus releasing the implant 10 at the desired site.

The entire operation is preferably monitored by radiography.

If it is desired to "recover" the implant 10 after release, the hook 35 of the first rod 30, and then, the second rod 40, are caused to pass into the ring 14 again, beyond its distal end 18. It is then possible to pull the wires and the catheter while holding the sleeve tightly (or to push on the sleeve 60 while holding the grip 70 tightly) in order to cause the implant 10 to return into the sleeve 60 by means of the hook 35 so that it resumes its radially closed state, as shown in FIG. 1.

According to another embodiment shown in FIGS. 6 and 7, the invention can also be applied to the implantation of a blood filter 110 comprising radially mobile limbs 115, such as, especially, the temporary/permanent filter of patent FR-A-2 718 949, in this case connected by its head 113 to the retention/release device 20. For that purpose the head 113 is provided with an orifice 116 that opens out, thus defining a tube 114. The orifice 116 may have a shoulder 117 against which the hook 35 can be supported in order to retain the filter in its radially closed state inside the sleeve 60, against the distal end 50b of the catheter 50.

The manoeuvring of the assembly so formed is the same as above.

Figure 8:
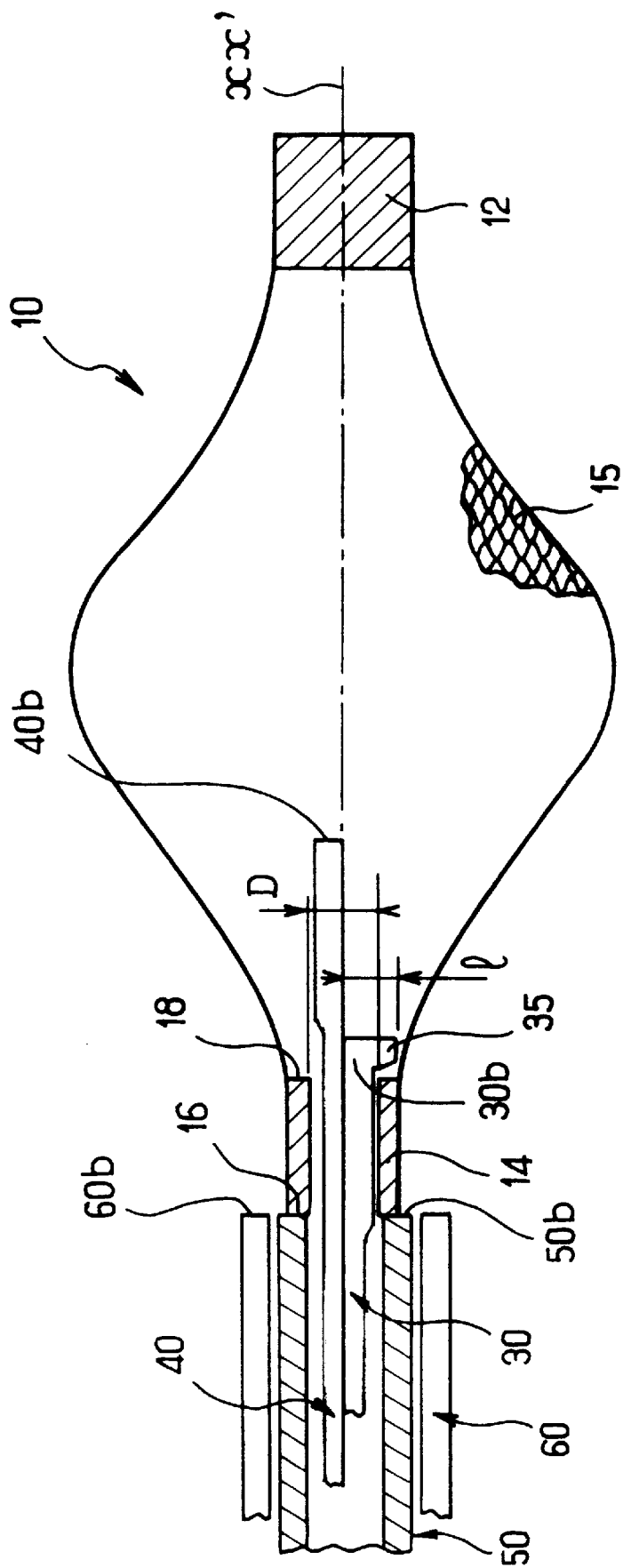
FIG. 8 is another variant of the device for positioning the implant.

Referring now to FIG. 8, it will be seen that the cross-section (in this case the diameter) of at least one (30 or 40) of the two wires used, and preferably of the two wires 30 and 40, is strictly smaller than the inside diameter of the sleeve 50 in which the wire(s) slide(s), with the optional exception, as shown, of the region near their distal end 30b and 40b where they preferably have a larger diameter, with the presence of a shoulder at the site of the change in diameter (a solution with a gradual variation in the diameter is also possible). Thus, the sum of the cross-sections of the two wires 30 and 40 is strictly smaller than the inside diameter of the catheter 50. That solution facilitates the relative movement of the wires 30 and 40 inside the sleeve 50, while avoiding too great a friction which could cause jamming or incorrect release of the implant. That configuration of the wires also enables the implant 10/110 to hook on correctly, especially owing to the fact that the portion of each wire located inside the tubular region 14/114 of the implant, when the implant is hooked onto the device in a positioning situation, has a larger cross-section than the rest of the wire and is therefore more rigid.

It should also be noted that the hook 35 may be in various shapes, for example in the shape of a fork or in a "V" shape.

Likewise, the rods 30 and 40 may have a cross-section in the shape of a semicircle, which enables the wires to be better centred and prevents the hook from turning on itself and being incorrectly positioned. It should also be mentioned that "elongate elements" is intended to mean, for example, rods that are solid, catheters or wires (straight or helical).

It is also possible to replace the ring 14 by any axially hollow region that can accommodate the two rods 30 and 40 and the protuberance 35, with the aim of retaining the implant 10 on its retaining device while enabling it to be released at the desired moment.

I claim:

1. Assembly for positioning an implant in an internal passageway of a body, wherein the implant has an axis, at least one axial tubular region having an inside diameter, and a structure suitable for adopting a first, radially deployed, state in a situation implanted in the passageway, or a second, radially restricted, state in a positioning situation, said assembly comprising a first and second removable elongated elements slidably mounted inside a catheter having an inside and an outside diameter, the first and second elements cooperating closely for positioning or withdrawing the implant, the first and second elements having a predetermined cross-section and extending substantially parallel to one another, the first element only having, towards the distal end, a lateral protuberance having a radial length, while the other element has no such protuberance, a cumulative cross-section dimensions of the two elements away from their distal end, and the radial length of the lateral protuberance, being smaller than the inside diameter of the tubular region of the implant so that the elements pass through at their distal end in a situation of positioning the implant in the passageway, the lateral protuberance of the first element being disposed outside the catheter when the implant is in its first radially deployed state while the assembly is still retaining the implant, and the radial length of the lateral protuberance being smaller than a inside diameter of the catheter so that, once the implant is released and in place in the passageway, the second element can be pulled through the catheter to be withdraw.

2. Assembly according to claim 1, wherein the first and second elongate elements are in the form of two long wires arranged slidably in a catheter with the protuberance of the first element then being located outside the catheter, the catheter and the wires being sufficiently long to be manoeuvred from outside the body, while the implant is in the passageway.

3. Assembly according to claim 2 further comprising a sleeve which has an inside diameter which is greater than the outside diameter of the catheter and of the tubular region of the implant and which is suitable for accommodating the implant in its radially restricted state, the catheter and the wires constituting a means of maneuver sufficiently rigid to provide for axial movement of the implant in order to position it in the passageway.

4. Assembly according to claim 2, wherein, when the implant is in its held position, while the distal end of the elongate elements is engaged through the tubular region of the implant, the catheter is placed substantially against a proximal surface of that region while the lateral protuberance of the first element is placed against a distal surface of said region.

5. Assembly according to claim 2, wherein at least one of the two wires has over most of its length a cross-section which is strictly smaller than half the inside diameter of the catheter, it being possible for the other wire to have over its entire length a cross-section smaller than or equal to half the inside diameter of the catheter, so that the sum of the cross-sections of the two wires is strictly smaller than the inside diameter of the catheter.

6. Assembly according to claim 5, wherein the two wires have a circular cross-section and each has a diameter strictly smaller than half the inside diameter of the catheter over their entire length with the exception of a region close to their distal end where their diameter is greater than or equal to half the inside diameter of the catheter.

7. Assembly according to claim 1, wherein the first element is in the form of a substantially rectilinear rod which is curved at its distal end, forming an angle of approximately from 45° to 90° with the rod, to form a short hook.

8. Assembly according to claim 1 further comprising a grip having a front end beyond which the elongated elements extend, each element being secured to an axial slide, and a first slide, to which the second element is secured, being arranged in front of that to which the first element is secured.

9. Assembly according to claim 8, wherein the first slide is provided with a manoeuvring arm in order to be accessible to the user's hand, while the second slide is not accessible from outside the grip.

10. Assembly according to claim 1, wherein the implant is a blood filter suitable for being implanted either temporarily or permanently, after the withdrawal of the holding/release device from the tubular region of the filter.

11. Assembly according to claim 1, wherein the implant is a vascular atherectomy or occlusion device.

* * * * *